United States Patent [19]

Hedin et al.

[11] Patent Number: 5,074,304

[45] Date of Patent: Dec. 24, 1991

[54] IMPLANTABLE HEART PACEMAKER AND METHOD FOR STIMULATING THE HEART WITH THE REPETITION RATE OF THE STIMULATIONS OF HEART MUSCLE CONTRACTIONS LIMITED TO A MAXIMUM VALUE

[75] Inventors: Asa Hedin, Stockholm; Jan Ljungstroem, Solna, both of Sweden

[73] Assignee: Siemens Aktiengesellschaft, Munich, Fed. Rep. of Germany

[21] Appl. No.: 477,533

[22] Filed: Feb. 9, 1990

[30] Foreign Application Priority Data

Feb. 10, 1989 [EP] European Pat. Off. ......... 89102348.3

[51] Int. Cl.$^5$ ............................................. A61N 1/368
[52] U.S. Cl. ............................................. 128/419 PG
[58] Field of Search ......... 128/419 PG, 419 D, 419 P

[56] References Cited

U.S. PATENT DOCUMENTS

| 4,554,921 | 11/1985 | Boute et al. | 128/419 PG |
| 4,856,523 | 8/1989 | Sholder et al. | 128/419 PG |
| 4,932,406 | 6/1990 | Berkovits | 128/419 PG |

FOREIGN PATENT DOCUMENTS 0147820 7/1985 European Pat. Off. .
0229613 1/1989 European Pat. Off. .

OTHER PUBLICATIONS

"Pulse Generator 704—Physician's Manual" (Mar. 1985 Siemens).

Primary Examiner—William E. Kamm
Assistant Examiner—Kennedy J. Schaetzle
Attorney, Agent, or Firm—Hill, Van Santen, Steadman & Simpson

[57] ABSTRACT

An implantable heart pacemaker includes a detector for natural heart muscle contractions in the region of the atrium and circuitry for stimulating heart muscle contractions in the region of the ventricle, the stimulating circuitry generating a stimulating pulse following the detection of a natural heart muscle contraction in the region of the atrium. The repetition rate of the pulses which stimulate heart muscle contractions in the region of the ventricle is limited to a maximum value which tracks and is not less than the heartbeat frequency adapted to the current physical activity of the pacemaker user.

8 Claims, 1 Drawing Sheet

IMPLANTABLE HEART PACEMAKER AND METHOD FOR STIMULATING THE HEART WITH THE REPETITION RATE OF THE STIMULATIONS OF HEART MUSCLE CONTRACTIONS LIMITED TO A MAXIMUM VALUE

BACKGROUND OF THE INVENTION

1. Field of the Invention

The present invention is directed to a heart pacemaker, and in particular to a heart pacemaker wherein ventricular stimulation occurs following the sensing of a natural atrial contraction, and which includes a sensor for a physiological parameter indicative of the physical activity of the pacemaker user and which uses the sensed parameter as a basis for limiting the rate of ventricular stimulation. A corresponding method is also disclosed.

2. Description of the Prior Art

A heart pacemaker commercially available from Siemens-Elema AB of Solna, Sweden is described in the publication "Pulse Generator 704—Physician's Manual" (March 1985). This pacemaker can operate in a number of different modes, including the DDD mode. In this operating mode, a heart muscle contraction in the region of the ventricle is stimulated, if needed, after the detection of a spontaneous (i.e., natural or non-pacemaker stimulated) heart muscle contraction in the region of the atrium. Ventricular stimulation occurs if no natural heart muscle contraction in the region of the ventricle appears during a time span, known as the A-V interval, which follows the detection of the spontaneous heart muscle contraction in the region of the atrium. In this operating mode, a heart muscle contraction in the region of the atrium is stimulated when a second time interval, referred to as the base interval, has elapsed without a spontaneous heart muscle contraction being detected in the region of the atrium. The generation of an atrial stimulation pulse activates both the base interval and the A-V interval. The repetition rate of the ventricular stimulations is limited to a maximum value, known as the highest synchronous rate (HSR). The highest synchronous rate is approximately 150 stimulations per minute.

The DDD operating mode is prescribed for various types of cardiac pathology, particularly for patients having A-V block. The DDD mode, however, is not utilized for patients who suffer fibrillations of the atrium which cannot be treated with medication. For these patients there is the risk that the heart muscle contractions which appear during fibrillation of the atrium will be detected and which, in view of the high repetition of the heart muscle contractions in the atrium during fibrillation, would result in the heart ventricle being artificially stimulated at a repetition rate which corresponds to the maximum value, i.e., to the HSR. In patients wherein the risk of atrial fibrillation is present, a conversion is generally made to the VVI operating mode, in which both the detection and stimulation of ventricular contractions occurs, with a ventricular contraction always being stimulated if no natural ventricular contraction is detected within a defined time interval.

In some patients, atrial fibrillation occurs intermittently. Nonetheless, the pacemaker must operate in the VVI mode for these patients, even though it would be desireable to permit the pacemaker to operate in the DDD mode as long as there is no atrial fibrillation.

In theory it is conceivable to detect atrial fibrillation and automatically to switch the heart pacemaker, normally operating in the DDD mode, to the VVI mode only during the appearance of fibrillation in the atrium. This conceptual approach, however, has significant practical problems. First, it is difficult to obtain the necessary faultless intracardial electrocardiogram of atrial activity which would be needed to accurately trigger the switch from the DDD mode to the VVI mode. Second, even if such an accurate atrial electrocardiogram could be obtained, an algorithm to identify atrial fibrillation would be needed, because of the pronounced changes in amplitude and large fluctuations in the heart rhythm which occur during atrial fibrillation could not be handled without clipping and/or distortion by conventional pacemaker components.

The same problems are present for other atrial synchronous operating modes of pacemakers.

SUMMARY OF THE INVENTION

It is an object of the present invention to provide a heart pacemaker, and a method for stimulating the heart, which can be employed without risk for patients who have intermittently appearing atrial fibrillation.

The above object is achieved in a heart pacemaker which includes means for identifying a heartbeat frequency corresponding to or indicative of the current physical activity of the pacemaker user, and mean for limiting the maximum repetition rate of the ventricular stimulations which tracks or follows the heartbeat frequency adapted to the sensed parameter, and is at least equal to that adapted heartbeat frequency. In contrast to conventional heart pacemakers, therefore, the heart pacemaker disclosed herein has a maximum value which is not a fixed value, but which is instead a value which varies dependent on the physical activity of the pacemaker user. Because the maximum value is at least equal to the heartbeat frequency adapted to the sensed physical activity, it is assured that the pacemaker user's heart can, as needed, be stimulated with a frequency adapted to the physical activity, and it is also insured that the maximum possible repetition rate of the artificial ventricular stimulations will be limited to a maximum value in the event of atrial fibrillation. Because the maximum value tracks or follows a heartbeat which corresponds to the sensed physical activity, the maximum value will not be unnecessarily high, but will instead be based on accurate physiological requirements. It is preferable, therefore, to set an upper limit for the maximum value which corresponds to a physiologically meaningful upper value of heartbeats, such as a rate, which corresponds to the heaviest physical activity which would be expected for a particular patient.

A further advantage of the heart pacemaker disclosed herein is that the risk of pacemaker-caused tachycardia is greatly reduced because the repetition rate of the ventricular stimulations is limited to a maximum value which is based on the physical activity of the pacemaker user and which does not significantly exceed this maximum value.

In a further embodiment of the invention, the means for limiting the repetition rate of the ventricular stimulations is set at a defined level slightly larger than the heartbeat frequency which is identified as corresponding to the sensed physical activity parameter. This insures that the ventricular stimulation repetition rate is not limited if the natural heartbeat frequency only slightly exceeds the identified, adapted heartbeat frequency. This insures that the fewest possible intrusions on the natural rhythm of the heart occur. The maximum value is preferably set at 5 to 15 heartbeats or pulses per minute above the natural heartbeat frequency which corresponds to the sensed physical activity.

The ventricular stimulation circuitry can undertake to provide ventricular stimulation pulses at a repetition rate equal to the heartbeat frequency associated with the sensed patient activity as soon as the repetition rate of the natural atrial contractions falls below the identified activity-related heartbeat frequency. This insures that, as needed, ventricular stimulation of the heart ensues at a repetition rate adapted to the physical activity of the pacemaker user, without additional technological outlay, because the identification of a heartbeat frequency adapted to the user's physical activity is already present. In a further embodiment, the pacemaker can provide pulses for artificially stimulating an atrial contraction, as needed, at a repetition rate corresponding to the identified heartbeat frequency, and the pacemaker can then stimulate a ventricular contraction following a stimulated atrial contraction. Thus each ventricular stimulation is preceded either by a natural or by a stimulated atrial contraction, as is physiologically correct, and both the atrial and ventricular stimulations will occur at a repetition rate corresponding to the identified heartbeat frequency corresponding to the physical activity of the patient.

A method for stimulating the heart is also disclosed which includes the steps of sensing natural atrial contractions, stimulating the ventricle following the detection of a spontaneous contraction in the atrium, sensing a physiological parameter indicative of the physical activity of the pacemaker user, identifying a heartbeat rate corresponding to the sensed level of activity, setting a maximum repetition rate which tracks the identified heartbeat rate and which is at least equal to the identified heartbeat rate, and limiting the repetition rate for ventricular stimulations to the maximum rate.

DESCRIPTION OF THE PREFERRED EMBODIMENTS

Figure 1:
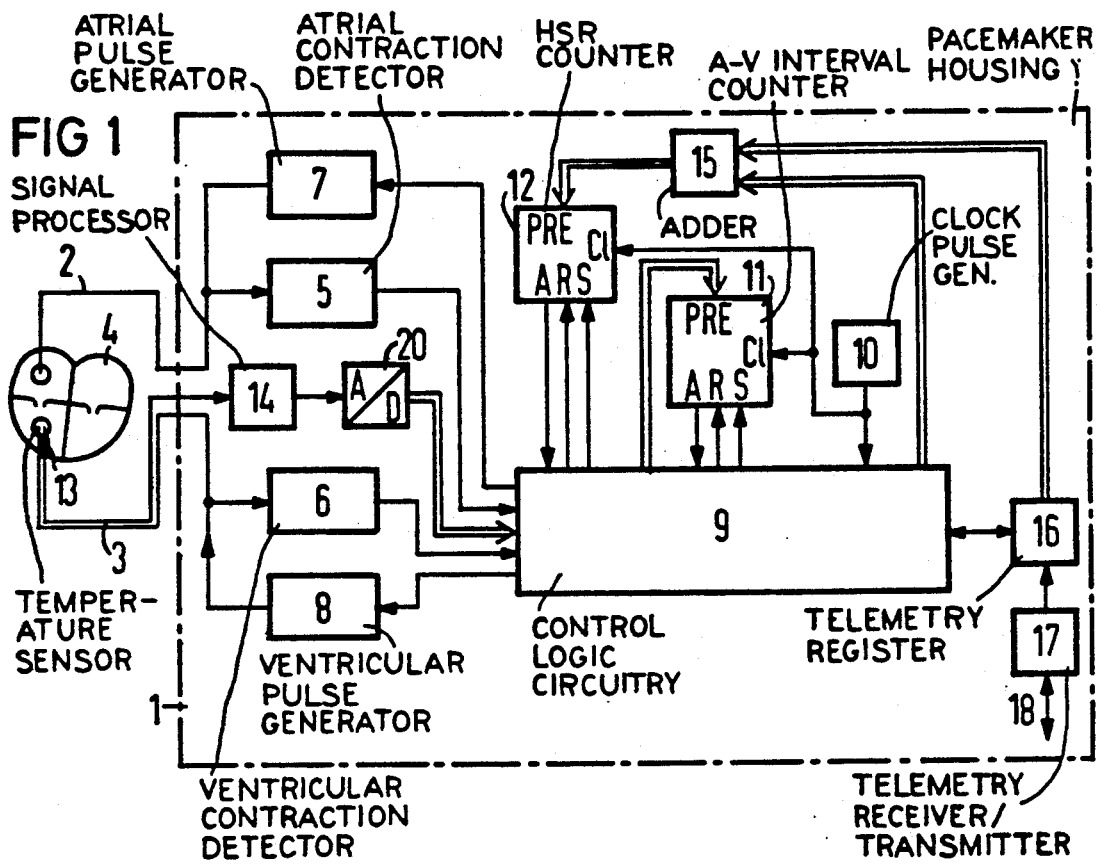
FIG. 1 is a schematic block diagram of a heart pacemaker constructed and operating in accordance with the principles of the present invention.

A heart pacemaker is shown in FIG. 1 which is constructed and which operates in accordance with the present invention. The pacemaker circuitry is contained in a hermetically sealed implantable housing 1. The circuitry is in electrical connection with two endocardial leads 2 and 3 each terminating in a known manner in an electrode. The lead 2 terminates and is anchored in the right atrium of the heart 4 of a patient in whom the pacemaker is implanted. The lead 3 terminates and is anchored in the right ventricle of the heart 4. The leads 2 and 3 may be conducted through the vein system of the patient to the heart 4.

The lead 2 is in electrical communication with a detector 5 which detects spontaneous (natural) heart muscle contractions in the region of the atrium. The lead 3 is in electrical communication with a detector 6 which detects spontaneous (natural) heart vessel contractions in the region of the ventricle. The leads 2 and 3 are also respectively connected to stimulation pulse generators 7 and 8. The stimulation pulse generator 7 provides pulses for stimulating heart muscle contractions in the region of the atrium. The stimulation pulse generator 8 generates pulses for stimulating heart muscle contractions in the ventricle.

The operation of the detectors 5 and 6 and the pulse generators 7 and 8 in combination with the heart 4 is controlled by logic circuitry 9 to which a clock generator 10, an A-V counter 11 and an HSR counter 12 are connected. The counters 11 and 12 are of the type known as preset counters. Each counter has a clock input Cl to which clock pulses are supplied, the counters 11 and 12 counting the number of clock pulses which occur during a counting event. A number which sets the count limit for each of the counters 11 and 12 is entered at the respective PRE inputs of the counters 11 and 12 (the count limit need not be the same for both counters 11 and 12). When the count limit is reached, each counter 11 and 12 generates a signal at an output A. Each counter 11 and 12 begins a counting event when enabled by a start pulse supplied to an input S. The counting event is aborted and/or the counter is reset if a reset pulse is supplied to an input R. In the pacemaker disclosed herein, both counters 11 and 12 receive their start and reset pulses from the control logic circuitry 9. Both counters 11 and 12 receive their clock pulses from the clock generator 10. The clock generator 10 is an oscillator, for example a crystal oscillator, which generates clock pulses at a defined clock frequency.

The operation of the heart pacemaker shown in FIG. 1 shall be set forth below only to such an extent as is required for explaining the present invention. Further details, not related to the invention disclosed and claimed herein, can be found in the aforementioned publication "Pulse Generator 704 — Physician's Manual."

When the detector 5 detects a spontaneous heart muscle contraction in the region of the atrium, a corresponding signal is supplied from the detector 5 to the control logic circuitry 9. In response, the control logic circuitry 9 starts the A-V counter 11, which receives clock pulses from the clock generator 10. When the A-V counter 11 has counted a number of clock pulses equal to the clock limit set via the input PRE from the control logic circuitry 9, a corresponding signal proceeds from the output of the counter 11 to the control logic circuitry 9. The counting limit for the counter 11 is reached at a time, following the generation of the start pulse, corresponding to the A-V interval. In response to the signal received from the counter 11, the control logic circuitry 9 generates a signal which enables the stimulation pulse generation 8 to generate a stimulation pulse which effects stimulation of a heart muscle contraction in the region of the ventricle, and which also resets the A-V counter 11. The generation of a stimulation pulse by the pulse generator 8 is suppressed, however, if the detector 6 has detected a spontaneous heart muscle contraction in the region of the ventricle during the A-V interval. If the control logic 9 receives a signal from the detector 6 before the count limit of the counter 11 (and thus the expiration of the A-V interval) is reached, it resets the A-V counter 11.

An interval known as the base interval also begins to run at the time an atrial contraction is detected. This interval is determined within the control logic circuitry 9, which is also supplied with clock pulses from the clock generator 10. If the detector 5 does not detect a spontaneous heart muscle contraction in the region of the atrium during the base interval (and thus no signal indicating such a spontaneous contraction is supplied to the control logic circuitry 9), the control logic circuitry 9 reaches the end of the base interval and enables the stimulation pulse generator 7 to generate a stimulation pulse which triggers a muscle contraction in the region of the atrium. Simultaneously with the generation of the pulse which actives the pulse generator 7, the control logic circuitry 9 starts the A-V counter again by supplying a signal to the input S thereto, and also begins the calculation of another base interval. If the A-V interval elapses without the detector 6 supplying a signal to the control logic circuitry 9 indicating the occurrence of a spontaneous ventricle contraction, the control logic circuitry 9 activates the stimulation pulse generator 8 to artificially stimulate a ventricular contraction.

If the detector 5 detects a spontaneous heart muscle contraction in the region of the atrium during the base interval, this results in the stimulation of a heart muscle contraction in the region of the ventricle in the manner described above by activation of the pulse generator 8 after expiration of the A-V interval, unless a spontaneous heart muscle contraction in the region of the ventricle is detected by the detector 6 during the A-V interval. The control logic circuitry 9 interrupts the ongoing count of the base interval upon the detection of a spontaneous atrial contraction occurring before the expiration of the base interval, and a new base interval count is started. The duration of the base interval thus establishes a lower limit below which the heartbeat frequency cannot drop.

Limitation of the repetition rate of the ventricular stimulations is achieved with the counter 12, which will be referred to as the HSR counter. The HSR counter 12 receives clock impulses from the clock generator 10. The HSR counter 12 is reset and started by the control logic circuitry 9 at respective inputs R and S upon each occurrence of a stimulation pulse to the ventricle generated by the pulse generator 8. The HSR counter 12 then counts a number of clock pulses which correspond to the duration of a time interval which must minimally elapse between two successive stimulations of heart muscle contractions in the ventricle. The heartbeat frequency corresponding to this time interval is usually referred to as the highest synchronous rate (HSR). As soon as this time interval has elapsed, a signal is supplied at the output A of the HSR counter 12, assuming the HSR counter 12 has not been reset. The HSR counter 12 is then reset and started again upon the occurrence of the next stimulation of a heart muscle contraction in the ventricle. It is thus possible to activate the ventricle stimulation pulse generator 8 only when the HSR counter 12 supplies a signal at output A, which in turn indicates that the count limit has been reached and thus the time interval corresponding to the HSR has elapsed. This means that at an artificial ventricular stimulation is omitted if the A-V interval ends during the counting operation of the HSR counter 12. Such a stimulation occurs, however, after the expiration of the time interval corresponding to the HSR. The repetition rate of artificial ventricular stimulations is thus limited to the HSR independently of the repetition rate of the heart muscle contractions in the region of the atrium.

In contrast to conventional pacemakers, wherein the HSR is programmable but, once programmed, has a fixed value during the normal operation of the pacemaker, the pacemaker disclosed herein sets a maximum value for the repetition rate of ventricular stimulations which corresponds to the HSR at all times, even when the HSR changes due to physical activity of the pacemaker user. For this purpose, a signal is obtained, as described in detail below, corresponding to the physical activity of the pacemaker user from which a heartbeat rate can be derived which corresponds to the user's current physical activity. The identification of this heartbeat frequency adapted to the physical activity permits the HSR to be set at a value at any given time which is at least equal to the heartbeat frequency adapted to the physical activity. Thus the pacemaker disclosed herein, even though it operates in the DDD mode, can also be employed without risk in patients who suffer intermittently appearing atrial fibrillation. This is because the HSR never reaches a value which is significantly higher than the heartbeat frequency (rate) which is adapted to the current physical activity of the patient. At the same time, the risk of pacemaker-induced tachycardia is considerably reduced. It is preferable that the maximum value for the ventricular stimulation repetition rate not be identical to the identified heartbeat frequency, but is set at a defined value greater than the identified heartbeat frequency.

Figure 2:
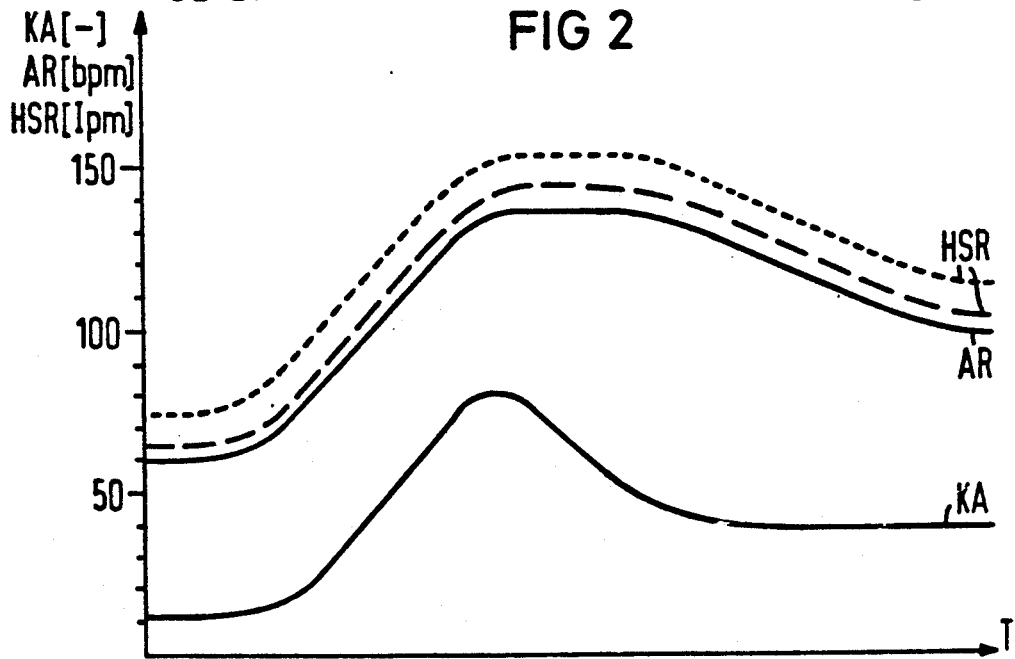
FIG. 2 is a graph showing curves for explaining the operation of the pacemaker of FIG. 1.

The corresponding relationships of these variables are shown in FIG. 2. A curve representing the physical activity KA of a patient is shown in FIG. 2, without the indication of a mass unit, as well as the heartbeat frequency AP (in heartbeats per minute bpm) adapted to the physical activity KA, and two different curves for the corresponding highest synchronous rate HSR (in impulses per minute IPM) over time T. In the example shown in FIG. 2, the physical activity KA of the patient initially rises from a relatively low level, reaches a maximum, and then drops and stabilizes at a slightly higher level than the initial level. The curve of the physical activity KA is followed or tracked by the adapted heartbeat frequency AR. The same is true for the highest synchronous rate HSR, which is shown slightly higher than the adapted heartbeat frequency AR by a defined amount of five heartbeats or pulses per minute shown by the dashed line curve, and by fifteen heartbeats or pulses per minute as indicated by the dotted curve.

To identify the heartbeat frequency adapted to the physical activity of the patient, a schematically indicated temperature sensor 13 is provided at the end of the lead 3 in the right ventricle of the heart 4, as shown in FIG. 1. The temperature sensor 13 measures the temperature of the venous blood in the right ventricle which, as is known, represents a measure for the physical activity of the patient. The temperature sensor 13 is in communication with a signal processing circuit 14, via a separate electrical line contained within the lead 3. The output of the processing circuit 14 is supplied to the control logic circuitry 9 via an analog-to-digital convertor 20. From the digital signal, the control logic circuitry 9 calculates the heartbeat frequency which corresponds to the measured physical activity of the patient according to an algorithm as disclosed, for example, in U.S. Pat. No. 4,543,954. The control logic circuitry 9 also calculates the number of clock pulses of the clock generator 10 which appear between two successive heartbeats, given this heartbeat frequency. The control logic circuitry 9 supplies data identifying this number of clock pulses to an adder 15, which adds a number of clock pulses to the number of clock pulses identified by the control logic circuitry 9, the added number of clock pulses corresponding to the number of heartbeats or impulses by which the HSR is intended to exceed the identified heartbeat frequency. The adder 15 supplies output data, corresponding to the sum of the two numbers of clock pulses, to the input PRE of the HSR counter 12. This sets the count limit for the HSR counter 12, and thus sets the limit for the HSR.

The control logic circuitry 9 internally uses the data indicating the number of clock pulses corresponding to the identified, physical activity-adapted heartbeat frequency, for setting the duration of the base interval. This results in the stimulation pulse generator 7, which supplies atrial stimulation pulses, operating at a repetition rate which corresponds to the identified, adapted heartbeat frequency in the event that the repetition rate of the detected, spontaneous atrial contractions falls below this adapted heartbeat frequency. As needed, the stimulation of a heart muscle contraction in the region of the ventricle by the pulse generator 8 follows an atrial stimulation after the expiration of the A-V interval. It is thus assured that the heartbeat frequency of the patient cannot fall below the heartbeat frequency which is adapted to the patient's current physical activity. The adapted heartbeat frequency may be limited within the control logic circuitry 9 to a lower limit of, for example, 60 heartbeats per minute, and to an upper limit of, for example, 140 heartbeats per minute. This insures that the adapted heartbeat frequency will always be within a physiologically meaningful region. This can be accomplished within the control logic circuitry 9 by undertaking a comparison of the heartbeat frequency obtained as a result of the physiological measurement with whatever upper and lower values are selected and supplying data corresponding to the lower limit to the adder 15 even if the derived frequency is below the lower limit, and supplying data corresponding to the upper limit to the adder 15 even if the derived frequency exceeds the upper limit.

As also shown in FIG. 1, the pacemaker may include a telemetry register 16 connected to the control logic circuitry 9, and a telemetry transmitter/receiver 17 connected to the telemetry register 16. The pacemaker is thus able to exchange data with an external programming device (not shown) as schematically indicated by the double arrow 18. It is thus possible to program many operating and sensing characteristics of the pacemaker. For example, different values for the duration of the A-V interval may be set using the programmer via the telemetry circuit 17 and via the telemetry register 16. These values are then supplied to the input PRE of the A-V counter via the control logic circuitry 9. It is also possible to telemetrically modify the amount by which the HSR exceeds the identified, physical activity-adapted heartbeat frequency. This is accomplished by supplying data corresponding to the desired (positive or negative) modification to an input of the adder 15. It is also possible to modify the upper and lower limit values for the activity adapted heartbeat frequency by re-programming these values in the control logic circuitry 9 via the telemetry components.

Although the pacemaker has been disclosed herein with reference to a pacemaker operating in the DDD mode, the inventive concept disclosed herein an be analogously employed in all atrial-synchronous heart pacemakers.

It is also possible to use a physiological parameter other than the temperature of venous blood in the right ventricle as the basis for determining the physical activity of the patient, and thus for determining the physical activity-adapted heartbeat frequency corresponding thereto. Many other parameters, and sensors adapted for detecting those parameters, are known to those in the art, and can be substituted for, or used in combination with, the temperature sensor 13.

It is also possible to omit the setting and counting of the base interval without departing from the inventive concept herein.

Although further modifications and changes may be suggested by those skilled in the art, it is the intention of the inventor to embody within the patent warranted hereon all changes and modifications as reasonably and properly come within the scope of her contribution to the art.

I claim as my invention:

1. An implantable heart pacemaker comprising:
   atrial activity detector means for detecting spontaneous heart muscle contractions in the region of the atrium of a pacemaker user;
   ventricular stimulation means for stimulating heart muscle contractions in the region of the ventricle of said pacemaker user at a ventricular stimulation repetition rate;
   means connected to said atrial activity detector means and to said ventricular stimulation means for controlling said ventricular stimulation means so that said ventricular stimulation means is enabled after detection of a heart muscle contraction in the region of the atrium by said atrial activity detector means;
   means for identifying a heartbeat frequency corresponding to the current level of physical activity of said pacemaker user; and
   means for limiting the maximum ventricular stimulation repetition rate of said ventricular stimulation means which tracks said heartbeat frequency so that said maximum ventricular stimulation rate is not less than said heartbeat frequency.

2. An implantable heart pacemaker as claimed in claim 1, wherein said means for limiting the maximum ventricular stimulation repetition rate is further defined as a means for limiting to a maximum value which is larger by a selected amount than said heartbeat frequency.

3. An implantable heart pacemaker as claimed in claim 1, wherein said means for identifying a heartbeat frequency is a means for sensing a physiological parameter of said pacemaker user indicative of the current level of physiological level of activity of said pacemaker user and which generates an activity signal corresponding to said level.

4. An implantable heart pacemaker as claimed in claim 1, further comprising:
   means for detecting if the ventricular stimulation rate of said ventricular stimulation means falls below said heartbeat frequency; and
   means for causing said ventricular stimulation means to stimulate heart muscle contractions at a rate corresponding to said heartbeat frequency if said ventricular stimulation repetition rate falls below said heartbeat frequency.

5. A heart pacemaker as claimed in claim 1, further comprising:

means for stimulating heart muscle contractions in the region of the atrium at said heartbeat frequency in the absence of a detected spontaneous heart muscle contraction by said atrial activity detector means;

ventricular activity detector means for detecting spontaneous heart muscle contractions in the region of the ventricle; and said means for controlling said ventricular stimulation means being connected to said ventricular activity detector means and enabling said ventricular stimulation means if no ventricular contraction is sensed by said ventricular activity detector means within a predetermined time following stimulation of said atrium by said atrial stimulation means.

6. A method for stimulating the heart of a patient comprising the steps of:

detecting spontaneous heart muscle contractions in the region of the atrium in the heart of said patient;

stimulating heart muscle contractions in the region of the ventricle of the heart of said patient only following the detection of a heart muscle contraction in the region of the atrium;

identifying a heartbeat frequency corresponding to the current level of physical activity of said patient; and limiting the maximum ventricular stimulation repetition rate to a value which is not less than said heartbeat frequency.

7. A method as claimed in claim 6, wherein the step of identifying a heartbeat frequency is further defined by the steps of:

sensing a physiological parameter of said patient which is indicative of the current level of physiological activity of said patient;

generating an electrical signal corresponding to the sensed parameter; and deriving said heartbeat frequency from said electrical signal.

8. A method as claimed in claim 6, wherein the step of limiting said maximum ventricular stimulation repetition rate is further defined by limiting said maximum ventricular stimulation repetition rate to a value which is greater than said heartbeat frequency by a selected amount.

* * * * *